United States Patent
Takahashi et al.

(10) Patent No.: US 11,006,820 B2
(45) Date of Patent: May 18, 2021

(54) FLEXIBLE TUBE INSERTION APPARATUS

(71) Applicant: OLYMPUS CORPORATION, Tokyo (JP)

(72) Inventors: Takeshi Takahashi, Hachioji (JP); Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 665 days.

(21) Appl. No.: 15/713,973

(22) Filed: Sep. 25, 2017

(65) Prior Publication Data
US 2018/0028049 A1  Feb. 1, 2018

Related U.S. Application Data

(63) Continuation of application No. PCT/JP2015/059409, filed on Mar. 26, 2015.

(51) Int. Cl.
*A61B 1/00* (2006.01)
*A61B 1/005* (2006.01)
(Continued)

(52) U.S. Cl.
CPC .......... *A61B 1/0056* (2013.01); *A61B 1/0051* (2013.01); *A61B 1/0057* (2013.01);
(Continued)

(58) Field of Classification Search
CPC . A61B 1/00078; A61B 1/0051; A61B 1/0053; A61B 1/0058; A61B 1/008
(Continued)

(56) References Cited

U.S. PATENT DOCUMENTS 4,329,980 A  5/1982 Terada
6,432,041 B1  8/2002 Taniguchi et al.
(Continued)

FOREIGN PATENT DOCUMENTS

EP  1 849 396 A1  10/2007
EP  2 583 616 A1  4/2013
(Continued)

OTHER PUBLICATIONS

Extended Supplementary European Search Report dated Nov. 12, 2018 in European Patent Application No. 15 88 6399.3.
(Continued)

*Primary Examiner* — Alexandra L Newton
(74) *Attorney, Agent, or Firm* — Scully, Scott, Murphy & Presser, P.C.

(57) ABSTRACT

An endoscope system includes an insertion section, a bending portion provided in the insertion section, including a distal side and a proximal side, and deformable into an arcuate shape by bending in at least one predetermined direction, a distal-side bending portion, a proximal-side bending portion, a first variable stiffness section provided in the distal-side bending portion and configured to change a stiffness of the distal-side bending portion, a second variable stiffness section provided in the proximal-side bending portion and configured to change a stiffness of the proximal-side bending portion, and a controller for performing control to make a stiffness of the first variable stiffness section higher than a stiffness of the second variable stiffness section.

25 Claims, 11 Drawing Sheets

(51) Int. Cl.
*A61B 1/06* (2006.01)
*A61B 5/06* (2006.01)
*A61B 1/31* (2006.01)

(52) U.S. Cl.
CPC ........ *A61B 1/00078* (2013.01); *A61B 1/0669* (2013.01); *A61B 5/065* (2013.01); *A61B 1/00006* (2013.01); *A61B 1/00009* (2013.01); *A61B 1/00045* (2013.01); *A61B 1/0052* (2013.01); *A61B 1/00117* (2013.01); *A61B 1/31* (2013.01)

(58) Field of Classification Search
USPC ........................................................ 600/144
See application file for complete search history.

(56) References Cited

U.S. PATENT DOCUMENTS

| | | | |
|---|---|---|---|
| 6,623,424 B2 | 9/2003 | Hayakawa et al. | |
| 2007/0038028 A1* | 2/2007 | Uchimura | A61B 1/0055 600/144 |
| 2012/0071722 A1 | 3/2012 | Nakamura et al. | |
| 2015/0305598 A1 | 10/2015 | Yamashita | |

FOREIGN PATENT DOCUMENTS

| | | |
|---|---|---|
| JP | 61-37931 A | 8/1986 |
| JP | 05-56910 A | 3/1993 |
| JP | 06-181882 A | 7/1994 |
| JP | 10-295629 A | 11/1998 |
| JP | 3927764 B2 | 6/2007 |
| JP | 2011-245180 A | 12/2011 |
| JP | 2012-65798 A | 4/2012 |
| JP | 2013-85744 A | 5/2013 |
| JP | 2015-002848 A | 1/2015 |
| NO | 2015/029503 A1 | 3/2015 |

OTHER PUBLICATIONS

Chinese Office Action dated Apr. 22, 2019 in Chinese Patent Application No. 201580078269.4.

Japanese Office Action dated Jul. 10, 2018 in Japanese Patent Application No. 2017-507286.

English translation of International Preliminary Report on Patentability dated Oct. 5, 2017 together with the Written Opinion received in related International Application No. PCT/JP2015/059409.

International Search Report dated Apr. 21, 2015 received in PCT/JP2015/059409.

Chinese Office Action dated Jun. 12, 2020 in Chinese Patent Application No. 201580078269.4

Japanese Office Action dated Mar. 30, 2021 received in 2020-069821.

* cited by examiner

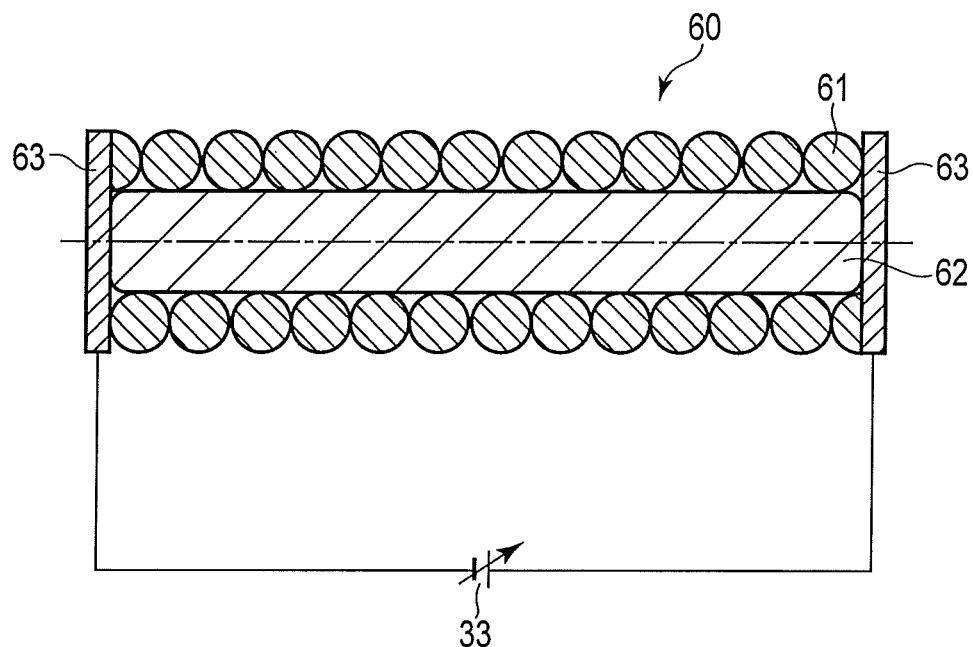
F I G. 3
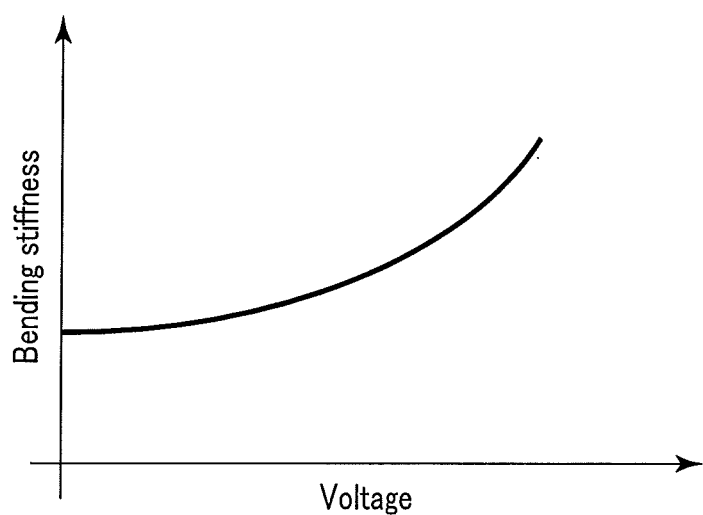
F I G. 4

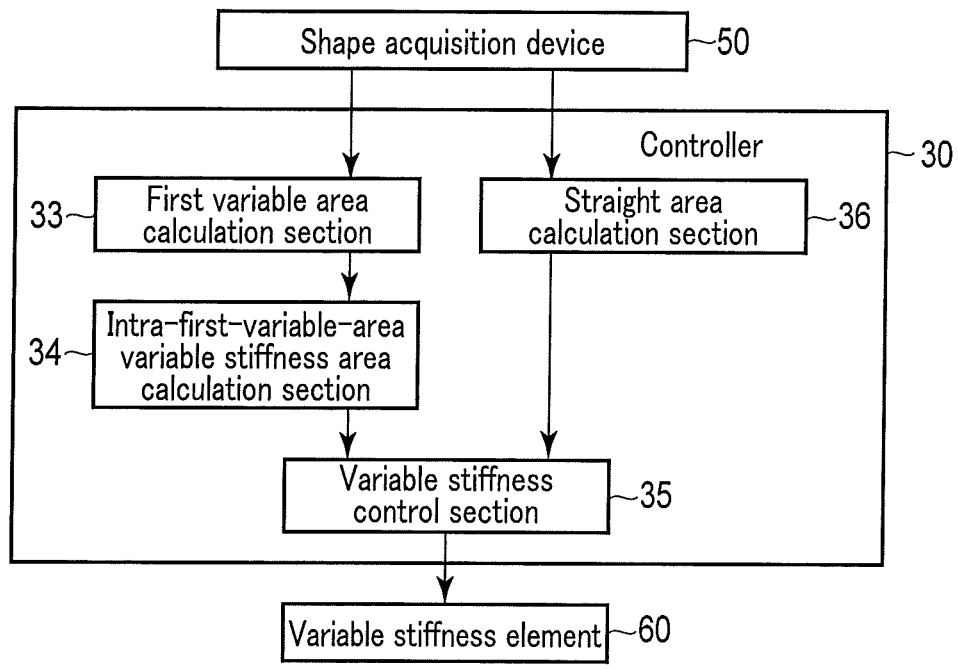
F I G. 8
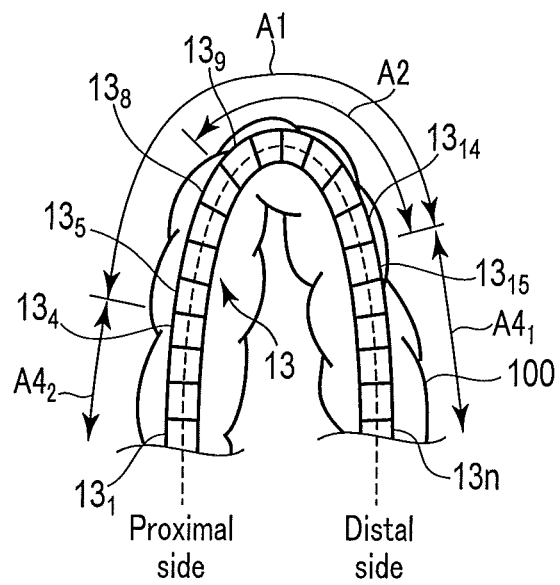
F I G. 9

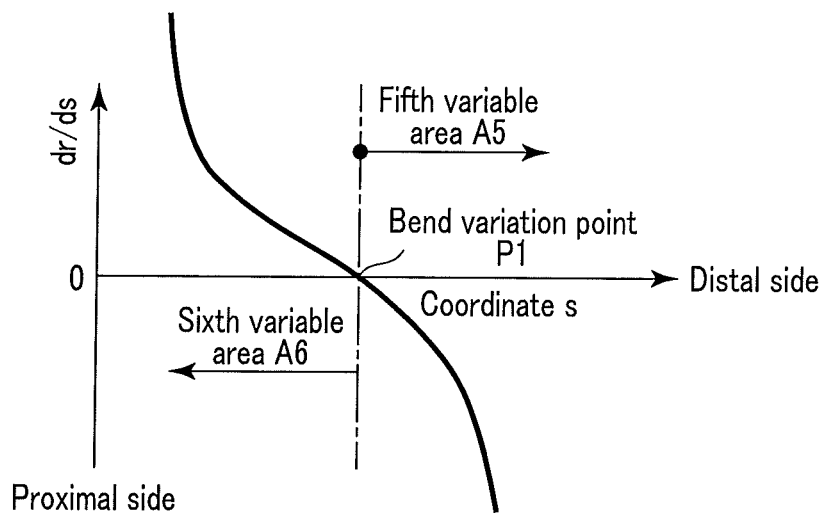
F I G. 14
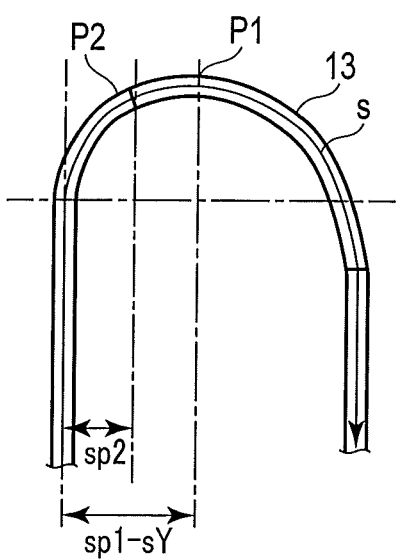
F I G. 15

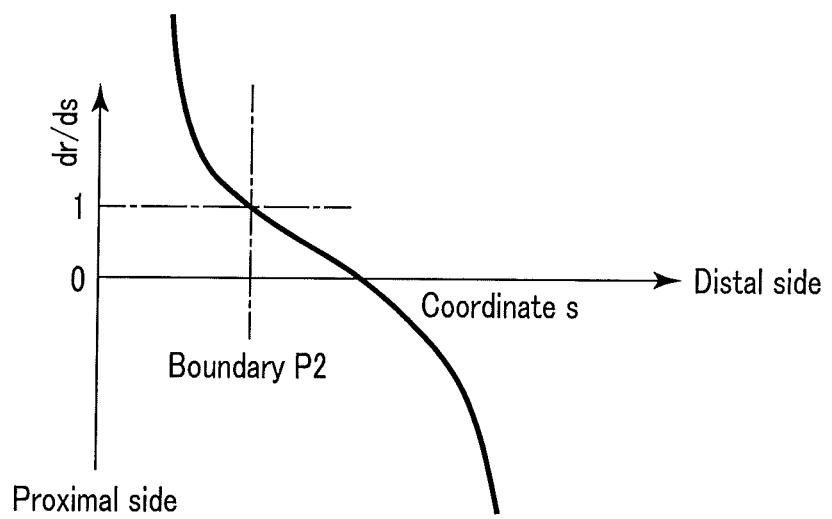
F I G. 18
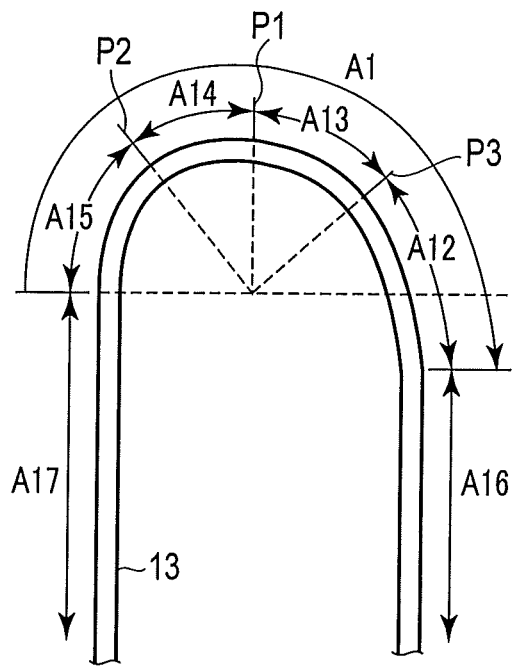
F I G. 19

FLEXIBLE TUBE INSERTION APPARATUS

CROSS-REFERENCE TO RELATED APPLICATIONS

This application is a Continuation application of PCT Application No. PCT/JP2015/059409, filed Mar. 26, 2015, the entire contents of all of which are incorporated herein by references.

BACKGROUND OF THE INVENTION

1. Field of the Invention

The present invention relates to a flexible tube insertion apparatus comprising an insertion section to be inserted into a subject.

2. Description of the Related Art

The large intestine roughly consists of the rectum, the colon, and the cecum from the side of the anus. The colon further consists of the sigmoid colon, the descending colon, the transverse colon, and the ascending colon from the rectum side. Normally, the sigmoid colon and the transverse colon are not fixed in the abdomen, and have freedom of movement. When a flexible, elongated insertion section (flexible tube portion) of a flexible tube insertion apparatus (e.g., an endoscope apparatus) is inserted into such an intestinal tract, the insertion section bends along the intestinal wall while passing through the intestinal tract. However, as the insertion section is further advanced from the hand side, the flexible insertion section may be bent in a direction different from the direction in which the force is applied in the intestine, preventing the distal end of the insertion section from passing smoothly. To address such a problem, a technique for facilitating transmission of a force to the direction in which the insertion section should desirably be inserted by increasing the bending stiffness of the insertion section is known. This is implemented either by increasing the bending stiffness of the insertion section itself, or by attaching a member different from the insertion section, such as an overtube (sliding tube), to the insertion section.

However, when the bending stiffness of the entire insertion section is uniformly changed, the stiffness cannot be changed according to the bending state of the insertion section inside the intestinal tract. Accordingly, the insertion section may be stuck in, for example, the sigmoid colon and excessively expand the sigmoid colon, causing distress to the patient. Such an insertion section is inconvenient for insertion into a deep portion.

Jpn. Pat. Appln. KOKOKU Publication No. 61-37931 discloses an elongated, flexible tube of an endoscope divided into a plurality of areas with different levels of flexibility, as viewed in the longitudinal direction. Japanese Patent No. 3927764 discloses a flexible tube for an endoscope in which easily bendable portions each having a locally short radius of curvature are intermittently arranged, and a portion having a radius of curvature longer than that of the easily bendable portions is arranged between the easily bendable portions, thus reducing the pressing force of the flexible tube against the inner wall of the lumen during insertion.

BRIEF SUMMARY OF THE INVENTION

One embodiment of the present invention is an endoscope system comprising an insertion section including a longitudinal axis, a bending portion provided in the insertion section, including a distal side and a proximal side along the longitudinal axis, and deformable into an arcuate shape by bending in at least one predetermined direction, a distal-side bending portion forming the distal side of the bending portion, a proximal-side bending portion provided continuously with the distal-side bending portion in the longitudinal direction and forming the proximal side of the bending portion, a first variable stiffness section provided in the distal-side bending portion and configured to change a stiffness of the distal-side bending portion, a second variable stiffness section provided in the proximal-side bending portion and configured to change a stiffness of the proximal-side bending portion, and a controller configured to perform control to make a stiffness of the first variable stiffness section higher than a stiffness of the second variable stiffness section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute apart of the specification, illustrate embodiments of the invention, and together with the general description given above and the detailed description of the embodiments given below, serve to explain the principles of the invention.

FIG. 3 is a diagram schematically showing an example of a configuration of a variable stiffness section.

FIG. 4 is a diagram showing a voltage-bending stiffness characteristic of the variable bending stiffness section.

FIG. 8 is a block diagram illustrating variable stiffness control according to a second embodiment.

FIG. 9 is a diagram showing an example of a first variable area, a second variable area, and a straight area of an insertion section (flexible tube portion) inserted into an intestinal tract according to the second embodiment.

FIG. 14 is a graph showing an example of a relationship between the coordinate of the insertion section and the first derivative of the radius of curvature.

FIG. 15 is a diagram schematically showing an example of a bending state of the insertion section (flexible tube portion) according to Variant 1 of the third embodiment.

FIG. 18 is a graph showing another example of a relationship between the coordinate of the insertion section and the first derivative of the radius of curvature.

FIG. 19 is an example diagram showing a plurality of variable stiffness areas set in a first variable area according to Variant 2 of the third embodiment.

DETAILED DESCRIPTION OF THE INVENTION

First Embodiment

The first embodiment of the present invention will be described with reference to FIGS. 1 to 7.

Figure 1:
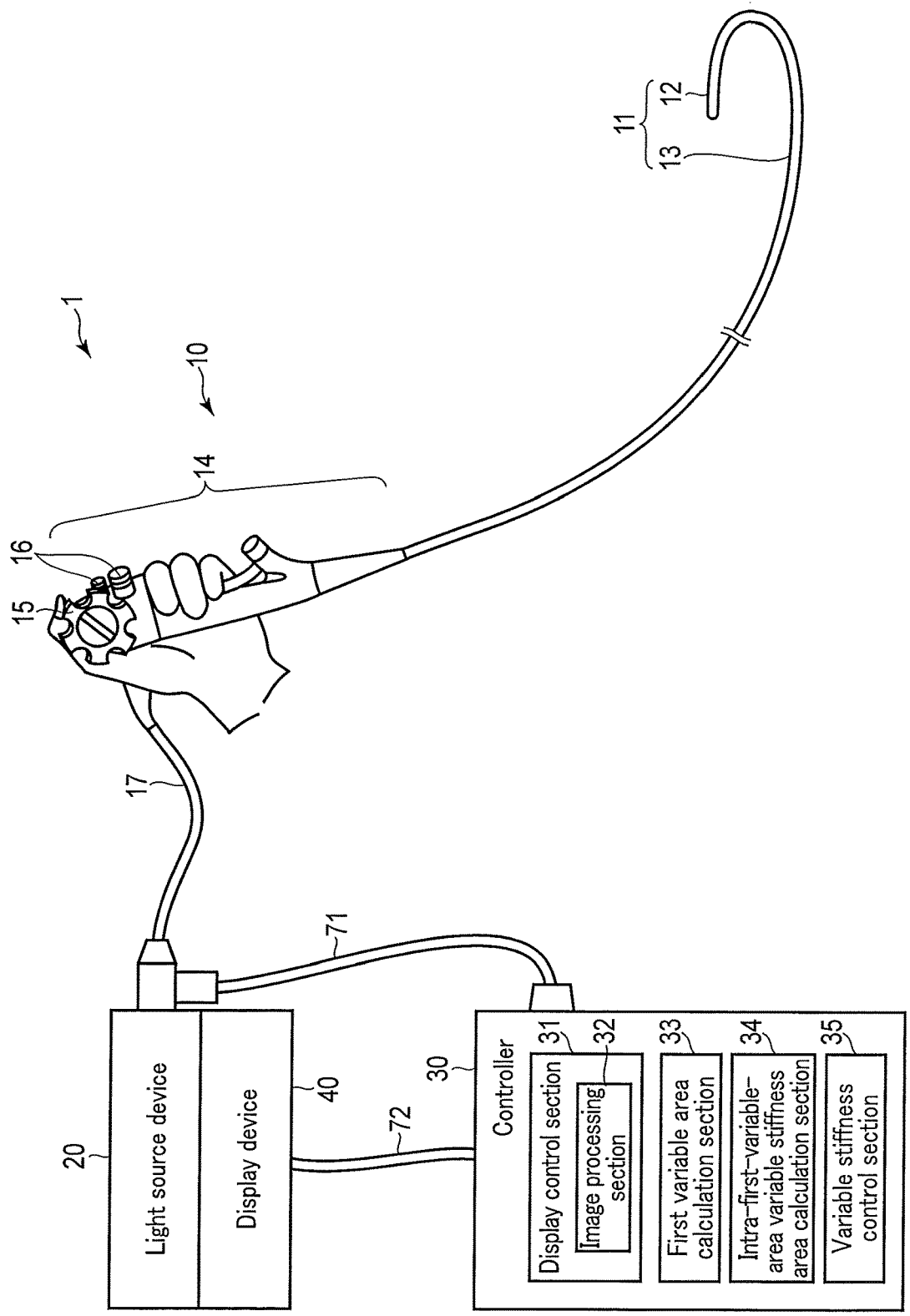
FIG. 1 is a diagram schematically showing a configuration of an endoscope apparatus.

FIG. 1 is a diagram schematically showing a configuration of an endoscope apparatus 1, which is a flexible tube insertion apparatus. The endoscope apparatus 1 comprises an endoscope 10, a light source device 20, a controller 30, a display device 40, and a shape acquisition device 50 (not shown in FIG. 1, see FIG. 2).

The endoscope 10 includes a tubular insertion section 11 to be inserted into a subject, and an operation section 14 provided on the proximal side of the insertion section 11. The endoscope 10 is, for example, a colonoscope. The insertion section 11 includes a distal portion 12 and a flexible tube portion 13 provided on the proximal side of the distal portion 12. The distal portion 12 incorporates, for example, an illumination optical system (illumination window), an observation optical system (observation window), an image sensor, and a bending portion that bends the distal portion, which are not shown in the drawings. The flexible tube portion 13 is an elongated tube that is bendable and flexible. The operation section 14 is provided with, for example, an angle knob 15 and switches 16, used for various operations including a bending operation and an imaging operation of the endoscope 10. The operation section 14 is the portion of the endoscope 10 that is gripped by the user, as shown in FIG. 1. A distal end of the distal portion 12 may be bent in any direction when the user operates the angle knob 15.

Figure 2:
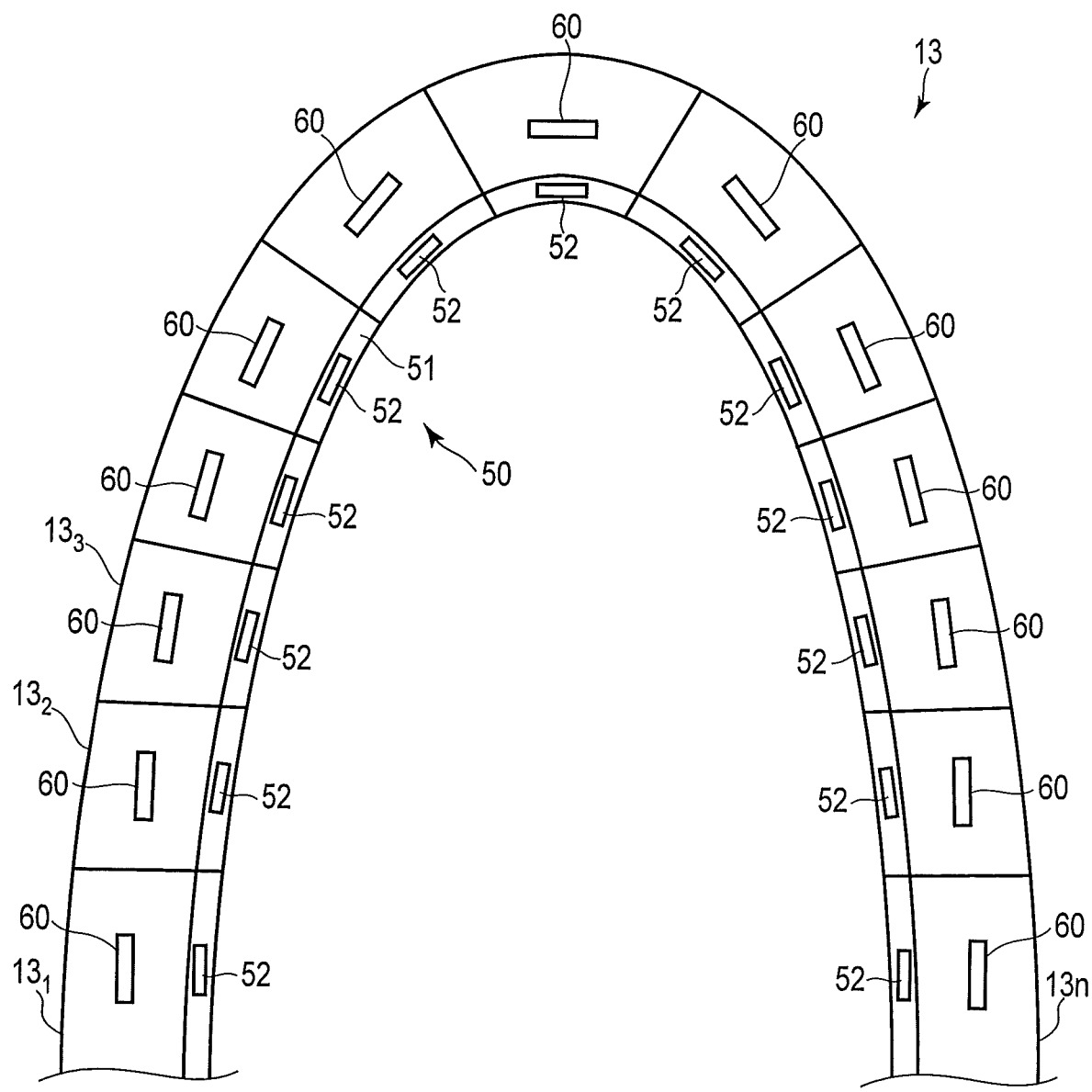
FIG. 2 is an enlarged view schematically showing a flexible tube portion.

FIG. 2 is an enlarged view schematically showing the flexible tube portion 13. For convenience, let us assume that the flexible tube portion 13 comprises a plurality of continuous segments (virtual units into which the flexible tube portion 13 is evenly divided as viewed in the longitudinal direction) defined in the longitudinal axis direction thereof. In FIG. 2, segments $13_1, 13_2, 13_3, \ldots,$ and $13_n$ of the flexible tube portion 13 are shown. A variable stiffness element 60 is provided in each of the segments. The variable stiffness element 60 is a variable stiffness actuator that can change the bending stiffness (stiffness) of the flexible tube portion 13 on a segment-by-segment basis. The flexible tube portion 13 includes at least a part of the shape acquisition device 50, which calculates the direction of each segment of the flexible tube portion 13 along its longitudinal axis in real time, and detects a change in the longitudinal axis direction. Details about the variable stiffness element 60 and the shape acquisition device 50 will be described later.

Referring back to FIG. 1, the endoscope 10 is connected to the light source device 20 via a universal cord 17 extending from the proximal side of the operation section 14. The universal cord 17 includes, for example, a light guide (optical fiber) connected to the illumination optical system, and an electric cable connected to the image sensor. The light source device 20 supplies light to be emitted from the illumination window of the distal portion 12 via the light guide.

The controller 30 is formed of a device including a CPU and the like. The controller 30 comprises a display control section 31 including an image processing section 32, a first variable area calculation section 33, an intra-first-variable-area variable stiffness area calculation section 34 (hereinafter referred to as an intra-area variable stiffness area calculation section 34), and a variable stiffness control section 35. The display control section 31 is connected to the electric cable in the universal cord 17 via a cable 71, and thus connected to the endoscope 10 (the imaging element of the distal portion 12). The display control section 31 is also connected to the display device 40 via a cable 72. The first variable area calculation section 33 is connected to the shape acquisition device 50, and the variable stiffness control section 35 is connected to the variable stiffness element 60 (see FIG. 5).

FIG. 3 is a diagram schematically showing an example of a configuration of the variable stiffness element 60. The variable stiffness element 60 includes a coil pipe 61 formed of a metal wire, an electroactive polymer artificial muscle (EPAM) 62 sealed in the coil pipe 61, and electrodes 63 provided on both ends of the coil pipe 61. The variable stiffness element 60 is connected to the variable stiffness control section 35, and thus a voltage may be applied from the variable stiffness control section 35 to the EPAM 62 in the coil pipe 61 via the electrodes 63. The EPAM 62 is an actuator that changes its stiffness and extends and contracts when a voltage is applied. The variable stiffness element 60 is incorporated into the flexible tube portion 13 in such a manner that the central axis of the coil pipe 61 coincides with or is parallel to the central axis of the flexible tube portion 13.

An electrode 63 (the EPAM 62) of the variable stiffness element 60 is applied with a voltage from the variable stiffness control section 35 via the cable 71 and an electric cable in the universal cord 17. When such a voltage is applied, the EPAM 62 tends to expand its diameter with the central axis of the coil pipe 61 at its center. However, the EPAM 62 is surrounded by the coil pipe 61, and is restrained from expanding its diameter. Accordingly, the bending stiffness (stiffness) of the variable stiffness element 60 increases as the value of the applied voltage increases, as shown in FIG. 4. That is, when the variable stiffness control section 35 changes the voltage applied to the variable stiffness element 60, the stiffness of the variable stiffness element 60 changes, and the bending stiffness of the flexible tube portion 13 incorporating the variable stiffness element 60 also changes.

The above-described configuration of the variable stiffness element 60 is an example. The variable stiffness element 60 does not need to use the EPAM 62, and may have any configuration that changes the bending stiffness in response to a control signal from the variable stiffness control section 35.

The shape acquisition device 50 is a bend sensor that calculates, in real time, the direction along the longitudinal axis of the flexible tube portion 13, in regard to each range of the flexible tube portion 13 in which at least the variable stiffness element 60 is arranged, and detects a change in the direction along the longitudinal axis. The shape acquisition device 50 may be configured of one of a sensor using electromagnetic waves (an electromagnetic sensor), a sensor using ultrasound waves (an ultrasonic sensor), a sensor using loss of light (an optical fiber sensor), a sensor using distortion (a distortion sensor), and a sensor using an X-ray absorbent material, or a combination thereof. Hereinafter, the shape acquisition device 50 embodied as a magnetic sensor will be described by way of example.

The shape acquisition device 50 includes an elongated probe 51 provided inside the flexible tube portion 13, as shown, for example, in FIG. 2. In the probe 51, a plurality of source coils 52 are provided to generate a magnetic field. The source coils 52 are arranged, for example, in the respective segments $13_1$, $13_2$, $13_3$, ..., and $13_n$ of the flexible tube portion 13 at intervals along the longitudinal axis direction of the flexible tube portion 13. The shape acquisition device 50 includes an antenna, not shown, for detecting a magnetic field generated by the source coils 52. The antenna is arranged around the periphery of the subject into which the endoscope 10 is inserted.

The probe 51 is connected to the controller 30, and an alternating-current signal is applied to the source coils 52 via the cable 71 and the electric cable that is inside the universal cord 17 from an alternating-current signal output section, not shown, of the controller 30. The antenna detects the magnetic field generated by the source coils 52, and outputs a detection signal to a shape calculation section, not shown, of the shape acquisition device 50. The shape calculation section calculates the bending shape of the flexible tube portion 13 on the basis of the received detection signal.

Next, the operation (colonoscopy) of the endoscope apparatus 1 will be described.

The insertion section 11 of the endoscope 10 is inserted by the user into an intestinal tract, which is a subject to be examined (from the anus through the rectum into the colon). The insertion section 11 passes through the intestinal tract while bending to follow the shape inside of the intestinal tract. The controller 30 controls the operation of the imaging element of the distal portion 12 of the insertion section 11 on the basis of the user's input operation to the operation section 14, and obtains an imaging signal output from the imaging element. The display control section 31 causes the image processing section 32 to generate an image of the interior of the large intestine on the basis of the obtained imaging signal. The display control section 31 causes the display device 40 to display the generated image.

Figure 5:
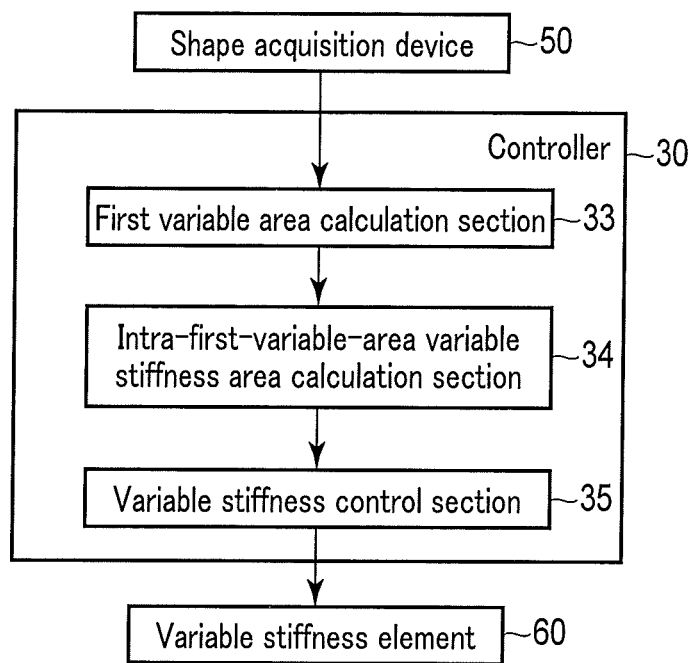
FIG. 5 is a block diagram illustrating variable stiffness control according to a first embodiment.

FIG. 5 is a block diagram illustrating variable stiffness control according to the first embodiment. The shape acquisition device 50 is constantly turned on while the endoscope apparatus 1 is used (while the insertion section 11 is inserted into the subject), and acquires real-time information about the bending shape of the flexible tube portion 13 during insertion. In other words, the shape acquisition device 50 constantly calculates the direction along the longitudinal axis direction of the flexible tube portion 13 in regard to each segment, and detects a change in the direction along the longitudinal axis direction.

When the shape acquisition device 50 is embodied as, for example, a magnetic sensor, the controller 30 sequentially applies an alternating-current signal to the source coils 52. Each of the source coils 52 generates a magnetic field around the periphery thereof. That is, information regarding the position of each source coil 52 is output from the source coil 52. The antenna detects the positional information of each source coil 52 on the basis of the output from the source coil 52, and the shape calculation section receives a detection signal. The shape calculation section constantly receives a detection signal during insertion, and calculates the bending shape of the flexible tube portion 13 inside an intestinal tract 100. The calculated bending shape may be displayed on the display device 40 via the display control section 31.

Let us assume that, at the start of insertion, the flexible tube portion 13 has a predetermined bending stiffness value (stiffness) that is neither the minimum bending stiffness value or the maximum bending stiffness value of the variable stiffness element 60. That is, the flexible tube portion 13 may be stiffened or softened, compared to the state at the start of insertion, by changing the bending stiffness of the variable stiffness element 60 on the basis of the control signal from the variable stiffness control section 35.

The bending shape of the flexible tube portion 13 calculated by the shape acquisition device 50 is output to the first variable area calculation section 33 of the controller 30. The first variable area calculation section 33 calculates an area (first variable area) A1, in which the direction along the longitudinal axis direction of the flexible tube portion 13 has changed, on the basis of the bending shape of the flexible tube portion 13 acquired from the shape acquisition device 50 (see FIG. 6).

The first variable area A1 is an area in which the direction along the longitudinal axis direction of the flexible tube portion 13 is bent along the shape of flexure of the intestinal tract at, for example, a predetermined curvature or larger, and is an area whose bending stiffness (stiffness) should be changed to facilitate insertion (passage) of the flexible tube portion 13. Since the bending stiffness of the flexible tube portion 13 can be changed by the variable stiffness elements 60 on a segment-by-segment basis, the first variable area A1 is set in units of segments. In the example shown in FIG. 6, the first variable area A1 includes 10 segments $13_5$ to $13_{14}$ of the flexible tube portion 13.

Figure 6:
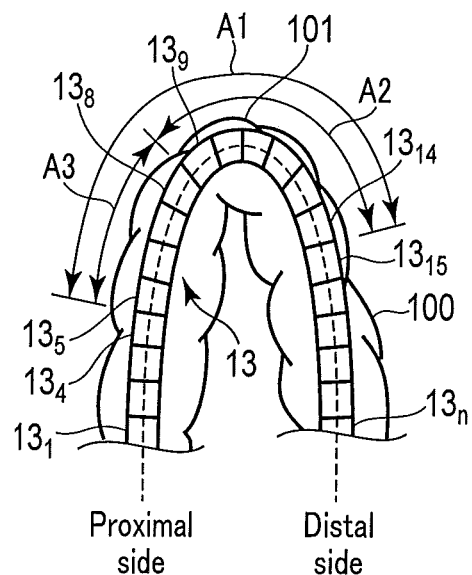
FIG. 6 is an example diagram showing a first variable area and a second variable area of an insertion section (flexible tube portion) inserted into an intestinal tract according to the first embodiment.

After the first variable area calculation section 33 calculates the first variable area A1, the intra-area variable stiffness area calculation section 34 calculates an area (second variable area) A2 whose bending stiffness should be further changed in the first variable area A1 (see FIG. 6). The second variable area A2 is an area in the first variable area A1 that should be set to have a bending stiffness different from that of the other part of the first variable area A1 (that should be further changed in bending stiffness). The second variable area A2 is also set in units of segments.

For example, the second variable area A2 is an area that starts at the first segment having a predetermined curvature or larger, counting from the most proximal segment of all the segments included in the first variable area A1, and ends at the most distal segment of all the segments included in the first variable area A1. Of the segments $13_5$ to $13_{14}$ included in the first variable area A1 shown in the example of FIG. 6, the second variable area A2 includes six segments $13_9$ to $13_{14}$, extending from the segment $13_9$, which is the first segment having a particularly large curvature (the first segment having a predetermined curvature or larger), counting from the most proximal segment $13_5$, to the most distal segment $13_{14}$.

The method for calculating the second variable area A2 in the first variable area A1 is not limited thereto. It is only required that the second variable area A2 is set in such a manner that a plurality of different stiffness areas (that do not completely match the first variable area A1) are provided in the first variable area A1.

After the first variable area A1 and the second variable area A2 are calculated, the variable stiffness control section 35 transmits, to the variable stiffness element 60, a control signal to control the bending stiffness of the first variable area A1 on a segment-by-segment basis. In the present embodiment, the bending stiffness of the second variable area A2 is controlled so as to be different from the bending stiffness of an area of the first variable area A1 that is not covered by the second variable area A2 (hereinafter referred to as a third variable area A3). Thus, the variable stiffness control section 35 controls the bending stiffness of the insertion section 11 (flexible tube portion 13) in such a manner that a plurality of different stiffness areas are generated in the first variable area A1.

For example, the variable stiffness control section 35 transmits, to the variable stiffness element 60, a control signal that increases an alternating-current signal applied to the variable stiffness element 60 of each of the segments $13_9$ to $13_{14}$ included in the second variable area A2, to increase the bending stiffness value of the second variable area A2. For example, the variable stiffness control section 35 transmits, to the variable stiffness element 60, a control signal that makes an alternating-current signal applied to the variable stiffness element 60 of each of the segments $13_5$ to $13_8$ included in the third variable area A3 smaller than an alternating-current signal applied to the variable stiffness element 60 of each of the segments $13_9$ to $13_{14}$ included in the second variable area A2. The bending stiffness value of each of the segments $13_5$ to $13_8$ included in the third variable area A3 should preferably be smaller than the bending stiffness value of each of the segments $13_1$ to $13_4$ and $13_{15}$ to $13_n$ not included in the first variable area A1.

The variable stiffness element 60 changes the bending stiffness of each of the segments $13_5$ to $13_{14}$ included in the first variable area A1 on the basis of the control signal from the variable stiffness control section 35. In the flexible tube portion 13 of the present embodiment, the bending stiffness value of each of the segments $13_9$ to $13_{14}$ included in the second variable area A2 is set to be high, and the bending stiffness value of each of the segments $13_5$ to $13_8$ included in the third variable area A3 is set to be minimum. This allows the third variable area A3 to be easily bent at a portion inside the intestinal tract having a large curvature and liable to extend. Since the second variable area A2 is set to have high stiffness, it is possible to prevent an unnecessary bend of the second variable area A2 or insufficient transmission of the force toward the direction of passage (distal side) when the insertion section 11 is inserted from the hand side.

The variable stiffness control shown in FIG. 5 is performed in real time during insertion of the insertion section 11 of the endoscope 10. The variable stiffness control shown in FIG. 5 is repeated on the basis of the bending shape of the flexible tube portion 13 acquired from the shape acquisition device 50.

For example, as the insertion section 11 passes through the large intestine, the first variable area A1 and the second variable area A2 (and the third variable area A3) are calculated as needed, and a control signal for changing the bending stiffness of each segment included in the areas is transmitted as needed from the variable stiffness control section 35 to the variable stiffness element 60. The segment of the flexible tube portion 13 located near an apex 101 of a flexure of the intestinal tract 100 shown in FIG. 6 changes from moment to moment with the passage of the flexible tube portion 13, and the first variable area A1 is constantly calculated (updated) by the first variable area calculation section 33. Accordingly, the segment located near the apex 101 of the flexure is always in the first variable area A1 and in the second variable area A2, and is set to have a high bending stiffness value. The third variable area A3 immediately following the second variable area A2 (on the proximal side) is always set to have a small bending stiffness value.

When the apex 101 of the flexure moves and changes in shape, the first variable area A1 and the second variable area A2 (and the third variable area A3) are calculated (updated) to follow the change in shape. Accordingly, the number of segments included in the first variable area A1 and the second variable area A2 is not always constant, and the optimum first variable area A1 and the optimum second variable area A2 are constantly calculated in accordance with the shape inside of the flexure of the intestinal tract 100, thus performing appropriate bending stiffness control for each area.

Figure 7:
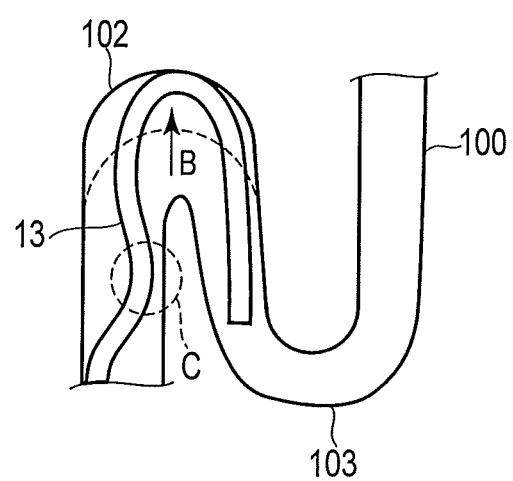
FIG. 7 is a diagram schematically showing extension of an intestinal wall by a flexible tube portion at an apex of a flexure of the sigmoid colon.

In the sigmoid colon, for example, the insertion direction of the insertion section 11 is the direction in which the insertion section 11 abuts against the flexure of the sigmoid colon, as shown in FIG. 7. The user inserts the insertion section 11 while moving the hand side to advance the insertion section 11 into a deep portion of the large intestine. However, if the overall bending stiffness of the flexible tube portion 13 is high, the flexible tube portion 13 may not be properly bent, causing the apex (S-top 102) of the flexure of the sigmoid colon to extend, as shown by the arrow B, from the state shown by the dotted line to the state shown by the solid line in FIG. 7. This causes distress to the patient. Even if the flexible tube portion 13 smoothly passes near the S-top 102, the same can happen near the flexure (SD junction SD-J 103) located behind the S-top 102 in the direction of passage.

In the present embodiment, the variable stiffness control section 35 controls the bending stiffness of the flexible tube portion 13 near the S-top 102 to reduce the patient's distress caused by the extension of the S-top 102. During insertion, the first variable area calculation section 33 and the intra-area variable stiffness area calculation section 34 constantly calculate the first variable area A1 and the second variable area A2 (third variable area A3) of the flexible tube portion 13, respectively, and the variable stiffness control section 35 performs real-time control of the bending stiffness of the areas A2 and A3. This allows the segment located near the S-top 102 (in front of the S-top 102) to constantly have a small bending stiffness value during passage of the insertion section 11, and to easily bend along the shape of flexure of the S-top 102. Thus, the force applied to the S-top 102 is reduced, or the excessive pressing force against the S-top 102 is reduced, thereby suppressing extension of the S-top 102.

According to the present embodiment, the bending stiffness of the variable stiffness element 60 may be changed in accordance with the bending shape of the insertion section 11 (flexible tube portion 13) inserted into a winding organ such as the large intestine, thus improving the ease of insertion of the insertion section 11. Moreover, since a plurality of different bending stiffness areas, such as an area with the lowest bending stiffness value (e.g., the third variable area A3) and an area with a higher bending stiffness value (e.g., the second variable area A2), are set in the bent first variable area A1, an unnecessary bend of the flexible tube portion 13 (e.g., at a portion C indicated by the dotted circle in FIG. 7) is prevented, thus providing an insertion section 11 (flexible tube portion 13) preferable for transmission of a force to the direction of passage. It is thus possible to provide a flexible tube insertion apparatus comprising an insertion section 11 with an improved ease of insertion.

Furthermore, the endoscope apparatus 1 comprises the shape acquisition device 50. This allows the controller 30 to constantly acquire information about the bending shape of the insertion section 11 (flexible tube portion 13) from the shape acquisition device 50, and perform variable stiffness control in real time. Thus, as the shape acquisition device 50 follows complex changes in the shape of the intestinal tract of, for example, the sigmoid colon and the transverse colon, on account of their freedom of movement in the abdomen, the bending stiffness of the flexible tube portion 13 can be suitably changed in accordance with their movement, thus further improving the ease of insertion. It is thus possible to provide a flexible tube insertion apparatus that is safe for patients and ensures the ease of insertion.

Hereinafter, the second and third embodiments of the present invention will be described. In the following, detailed explanations of the structures and operations similar to those in the first embodiment will be omitted, and only matters different from those of the first embodiment will be described. It is to be noted that the second embodiment and the third embodiment may be combined.

Second Embodiment

The second embodiment of the present invention will be described with reference to FIGS. 8 and 9.

In the second embodiment, the controller 30 includes a straight area calculation section 36, in addition to the display control section 31 including the image processing section 32, the first variable area calculation section 33, the intra-area variable stiffness area calculation section 34, and the variable stiffness control section 35. The straight area calculation section 36 is connected to the shape acquisition device 50. In the present embodiment, the bending shape of the flexible tube portion 13 acquired by the shape acquisition device 50 is output to the first variable area calculation section 33 and the straight area calculation section 36 of the controller 30.

FIG. 8 is a block diagram illustrating variable stiffness control according to the second embodiment. During insertion, the first variable area calculation section 33 acquires information about the bending shape of the flexible tube portion 13 inside the intestinal tract 100 constantly (in real time) from the shape acquisition device 50. Likewise, the straight area calculation section 36 constantly acquires information about the bending shape of the flexible tube portion 13 from the shape acquisition device 50.

The first variable area calculation section 33 and the intra-area variable stiffness area calculation section 34 calculate the first variable area A1 and the second variable area A2 in a manner similar to the first embodiment. In the present embodiment, the straight area calculation section 36 calculates fourth variable areas (straight areas) $A4_1$ and $A4_2$ (see FIG. 9), which are substantially straight areas of the flexible tube portion 13, on the basis of the bending shape of the flexible tube portion 13 acquired from the shape acquisition device 50, concurrently with the calculation of the first variable area A1 by the first variable area calculation section 33 and the calculation of the second variable area A2 by the intra-area variable stiffness area calculation section 34. A substantially straight area refers to, for example, an area that has a curvature less than a predetermined value, or that is regarded as a substantially straight line. The straight areas $A4_1$ and $A4_2$ are set in units of segments, as in the case of the first variable area A1 and the second variable area A2. In the example shown in FIG. 9, the straight area $A4_1$ includes segments $13_1$ to $13_4$, and the straight area $A4_2$ includes segments $13_{15}$ to $13_n$.

After calculation of the first variable area A1, the second variable area A2, and the straight areas $A4_1$ and $A4_2$, the variable stiffness control section 35 transmits, to the variable stiffness element 60, a control signal for controlling the bending stiffness of each of the second variable area A2, the third variable area A3, and the straight areas $A4_1$ and $A4_2$ on a segment-by-segment basis. In this case, the straight areas $A4_1$ and $A4_2$ are set to have a bending stiffness value higher than the third variable area A3 having the minimum bending stiffness value in the first variable area A1. Assuming that the minimum bending stiffness value in the first variable area A1 is K, the bending stiffness value of the straight area $A4_1$ is K1, and the bending stiffness value of the straight area $A4_2$ is K2, K<K1, and K<K2. The bending stiffness value K1 of the straight area $A4_1$ and the bending stiffness value K2 of the straight area $A4_2$, which may be the same or different, are set to be higher than the minimum bending stiffness value in the first variable area A1.

The variable stiffness element 60 changes the bending stiffness of the segments $13_1$ to $13_4$ and $13_{15}$ to $13_n$ included in the straight areas $A4_1$ and $A4^2$, as well as the bending stiffness of the segments $13_9$ to $13_{14}$ included in the second variable area A2 and the bending stiffness of the segments $13_5$ to $13_8$ included in the third variable area A3, on the basis of the control signal from the variable stiffness control section 35. This allows the segments $13_1$ to $13_4$ and $13_{15}$ to $13_n$ included in the straight areas $A4_1$ and $A4_2$ to be stiffened.

It is found that, during insertion, the insertion section 11 (flexible tube portion 13) transmits a force (insertion force) to the insertion direction (distal direction) more easily when the insertion section 11 is substantially straight except for the portion that is bent along the intestinal tract 100. Thus, in the present embodiment, the variable stiffness control section 35 controls the corresponding variable stiffness element 60 in real time, in such a manner that the bending stiffness value of the segments of the flexible tube portion 13 calculated by the straight area calculation section 36 as being substantially straight is higher than the bending stiffness value (minimum bending stiffness value) of the first variable area A1. That is, in the first embodiment, only the bending stiffness of the segments included in the first variable area A1 (the second variable area A2 and the third variable area A3) is changed, in regard to the area not included in the first variable area A1. In the second embodiment, the bending stiffness of the segments included in the straight areas $A4_1$ and $A4_2$ not included in the first variable area A1, as well as the bending stiffness of the segments included in the first variable area A1 (the second variable area A2 and the third variable area A3), is changed. This not only improves the ease of insertion into the S-top 102, but also facilitates transmission of the force toward its distal direction during insertion of the insertion section 11. It is also possible to suppress an unnecessary bend of the insertion section 11 in a portion that is not bent (see the dotted circle C shown in FIG. 7).

According to the present embodiment, the straight area calculation section 36 calculates a substantially straight area of the flexible tube portion 13 on the basis of the bending shape of the insertion section 11 (flexible tube portion 13)

acquired from the shape acquisition device 50, thus allowing the variable stiffness control section 35 to perform control to change the bending stiffness of the area (first variable area A1) in which the direction along the axial direction of the insertion section 11 has changed, but also the substantially straight area. By stiffening the substantially straight area, the force can be efficiently transmitted during insertion, and the ease of insertion is improved.

Third Embodiment

The third embodiment of the present invention will be described with reference to FIGS. 10 and 11.

In the third embodiment, the controller 30 includes a variation point calculation section 37 that calculates a point (e.g., an apex or an inflection point of the bend) at which the bending state has changed in the first variable area A1, in addition to the display control section 31 including the image processing section 32, the first variable area calculation section 33, the intra-area variable stiffness area calculation section 34, and the variable stiffness control section 35.

Figure 10:
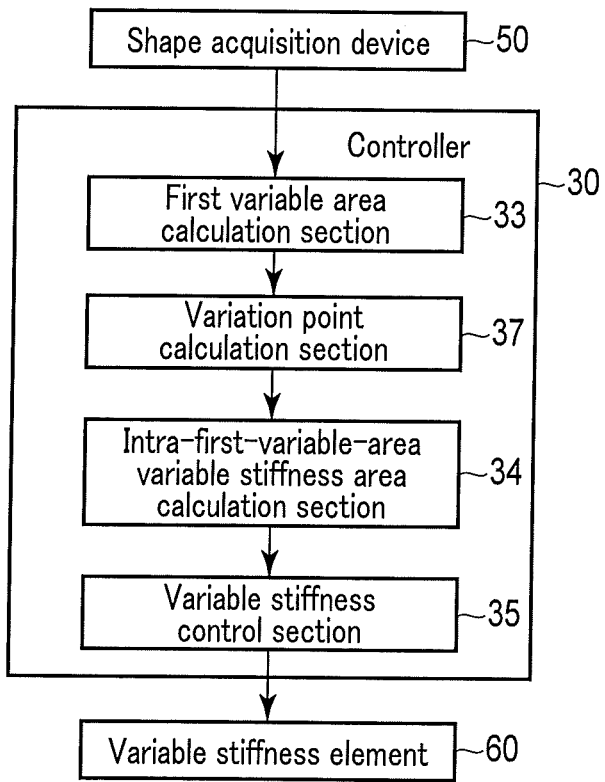
FIG. 10 is a block diagram illustrating variable stiffness control according to a third embodiment.
Figure 11:
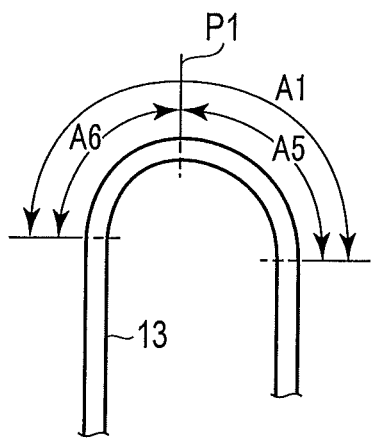
FIG. 11 is a diagram showing an example of a bend variation point, a fifth variable area, and a sixth variable area, which are calculated from within the first variable area, according to the third embodiment.

FIG. 10 is a block diagram illustrating variable stiffness control according to the third embodiment. During insertion, the first variable area calculation section 33 acquires information about the bending shape of the flexible tube portion 13 inside the intestinal tract 100 constantly (in real time) from the shape acquisition device 50. The first variable area calculation section 33 calculates the first variable area A1 on the basis of the acquired bending shape of the flexible tube portion 13.

In the present embodiment, after the first variable area calculation section 33 calculates the first variable area A1, the variation point calculation section 37 calculates a characteristic point (bend variation point) P1, at which the bending shape of the flexible tube portion 13 has changed, from within the first variable area A1. In the example shown in FIG. 11, the bending shape of the flexible tube portion 13 in the first variable area A1 may be expressed in two dimensions and fit using a function such as a quadratic function, and the position of the bend variation point (e.g., an apex) P1 is obtained. The number of bend variation points included in the first variable area A1 is not limited to one, and a plurality of bend variation points may be included. The bend variation point may be any point that can be calculated as a change in the bending shape, such as an apex and an inflection point.

After the variation point calculation section 37 calculates the bend variation point P1 from within the first variable area A1, the intra-area variable stiffness area calculation section 34 calculates a fifth variable area A5 and a sixth variable area A6 from within the first variable area A1, on the basis of information about the first variable area A1 and the bend variation point P1. The fifth variable area A5 and the sixth variable area A6 are also set in units of segments. In the example shown in FIG. 11, the fifth variable area A5 is an area that starts at the segment including the bend variation point P1 in the first variable area A1, and ends at the most distal segment of all the segments included in the first variable area A1. The sixth variable area A6 is an area that starts at the most proximal segment of all the segments included in the first variable area A1, and ends at a proximal-side segment adjacent to the segment including the bend variation point P1 in the first variable area A1. Thus, the intra-area variable stiffness area calculation section 34 calculates the fifth variable area A5 and the sixth variable area A6, in place of the second variable area A2 (and the third variable area A3).

After the intra-area variable stiffness area calculation section 34 calculates the fifth variable area A5 and the sixth variable area A6, the variable stiffness control section 35 transmits, to the variable stiffness element 60, a control signal for controlling the bending stiffness of the fifth variable area A5 and the sixth variable area A6 on a segment-by-segment basis. In the present embodiment, the bending stiffness value of the fifth variable area A5 at the distal side is set to be higher than the bending stiffness value of the sixth variable area A6 at the proximal side. That is, assuming that the bending stiffness value of the fifth variable area A5 is K5, and the bending stiffness value of the sixth variable area A6 is K6, K5>K6.

The variable stiffness element 60 changes the bending stiffness of the segments included in the fifth variable area A5 and the bending stiffness of the segments included in the sixth variable area A6 on the basis of the control signal from the variable stiffness control section 35. This makes the stiffness of the fifth variable area A5 higher than that of the sixth variable area A6 in the first variable area A1.

The fifth variable area A5 may be set to cover a range of segments that are regarded as having a substantially equal radius of curvature in the first variable area A1. In this case, the fifth variable area A5 is an area extending from the most distal segment of all the segments included in the first variable area A1 to the segment having a radius of curvature substantially equal to that of the most distal segment, and the sixth variable area A6 is an area including the segments on the proximal side relative to the fifth variable area A5 in the first variable area A1. The bend variation point P1 is the first point where the radius of curvature changes, counting from the distal side, in the first variable area A1.

Likewise, the sixth variable area A6 may be set to cover a range of segments that are regarded as having a substantially equal radius of curvature in the first variable area A1. In this case, the sixth variable area A6 is, for example, an area extending from the most proximal segment of all the segments included in the first variable area A1 to the segment having a radius of curvature substantially equal to that of the most proximal segment, and the fifth variable area A5 is an area including the segments on the distal side relative to the sixth variable area A6 in the first variable area A1. The bend variation point P1 is the first point where the radius of curvature changes, counting from the proximal side, in the first variable area A1. Thus, at least one of the fifth variable area A5 and the sixth variable area A6 may be set to cover a range of segments that are regarded as having a substantially equal radius of curvature in the first variable area A1.

Figure 12:
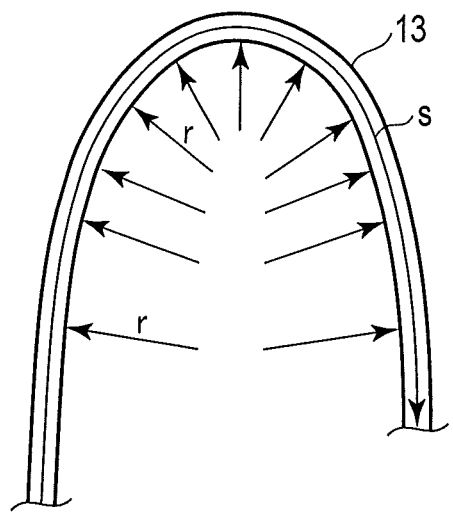
FIG. 12 is a diagram schematically showing an example of a bending state of an insertion section (flexible tube portion) according to the third embodiment.
Figure 13:
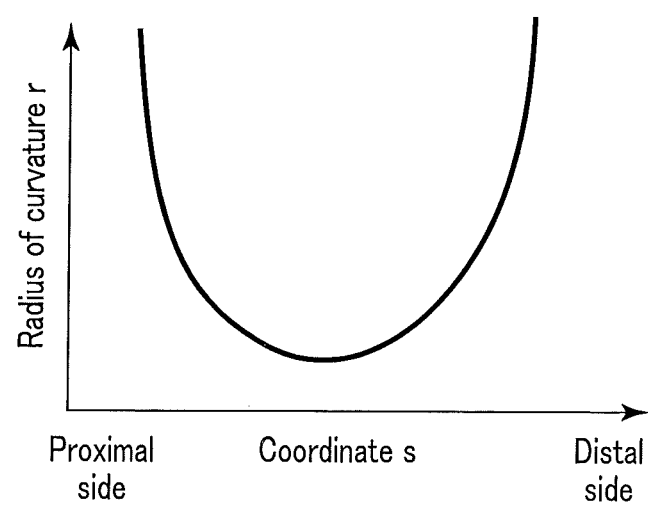
FIG. 13 is a graph showing an example of a relationship between a coordinate and a radius of curvature of the insertion section.

In the flexible tube portion 13 (insertion section 11) shown in FIG. 12, let us assume that the radius of curvature of the flexible tube portion 13 is r, and the coordinate going from the proximal side toward the distal side along the central axis of the flexible tube portion 13 is s. When the flexible tube portion 13 is bent, the proximal end of the flexible tube portion 13 is substantially straight, and has a radius of curvature that is close to ∞ and is reduced toward the bend variation point of the coordinate s. The radius of curvature increases again after the coordinate s passes through the bend variation point, and the flexible tube portion 13 becomes substantially straight again as the coordinate approaches the distal end of the flexible tube portion 13. FIG. 13 is a graph showing an example of a relationship between the coordinate s and the radius of curvature r of the flexible tube portion 13. Thus, the radius of curvature r is close to ∞ in a portion where the flexible tube portion 13 is straight, and is reduced toward the bend variation point. The radius of curvature r becomes minimum at the bend variation point, increases again, and comes close to ∞. Thus, as shown in FIG. 14, the bend variation point P1 may be calculated by assuming that, in the first variable area A1, the derivative dr/ds>0 is satisfied in the sixth variable area, and the derivative dr/ds≤0 is satisfied in the fifth variable area A5.

Various approaches show that the force that bends the flexible tube portion 13 during insertion is reduced when the hand side (proximal side) of the flexible tube portion 13 is soft, and that the force is transmitted to the distal side more easily when the distal side has a stiffness higher than that of the proximal side. Thus, according to the present embodiment, the variation point calculation section 37 calculates the bend variation point P1, and thereby the intra-area variable stiffness area calculation section 34 divides the first variable area A1 into the fifth variable area A5 including the segments on the distal side relative to the bend variation point P1 and the sixth variable area A6 including the segments on the proximal side relative to the bend variation point P1. The variable stiffness control section 35 controls the variable stiffness element 60 of each area in such a manner that the bending stiffness value of the proximal side is lower than the bending stiffness value of the distal side.

According to the present embodiment, at least by calculating two variable stiffness areas separated by the bend variation point P1 as a boundary in the first variable area A1 and setting the bending stiffness of one of the two variable stiffness areas that is at the distal end to be higher than the other, it is possible to more easily transmit the pressing force from the hand side to the distal side. It is thus possible to provide a flexible tube insertion apparatus that reduces the pressing force against the intestinal wall during insertion, and is safe for patients and ensures the ease of insertion.

Third Embodiment: Variant 1

In the third embodiment, the bend variation point P1 is used as a boundary between the fifth variable area A5 and the sixth variable area A6. However, the boundary P2 between the fifth variable area A5 and the sixth variable area A6 is not limited to the bend variation point P1. The boundary P2 may be calculated by the variation point calculation section 37 as will be described below.

(Calculation Method 1)

Figure 16:
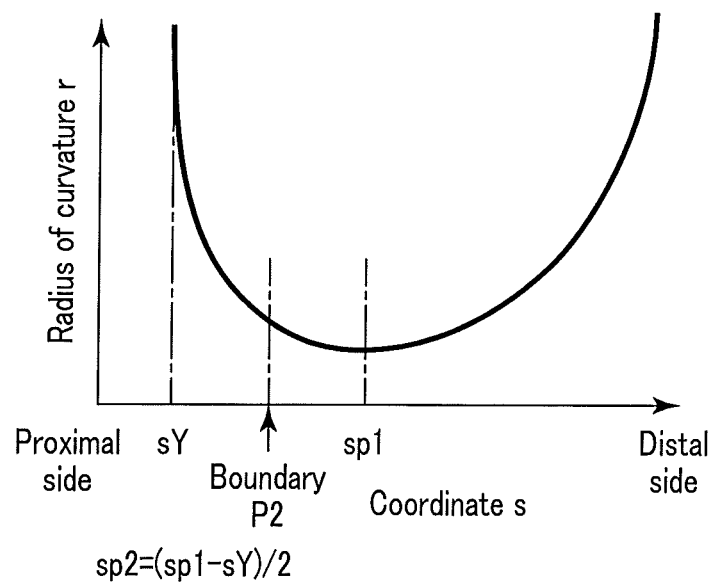
FIG. 16 is a graph showing another example of a relationship between the coordinate and the radius of curvature of the insertion section.

First, the bend variation point P1 is obtained. Assuming that the radius of curvature of the flexible tube portion 13 shown in FIG. 15 is r, and the coordinate going from the proximal side toward the distal side along the central axis of the flexible tube portion 13 is s, the position of the coordinate s at which the radius of curvature becomes minimum is the coordinate s (sp1) of the bend variation point P1. FIG. 16 is a graph showing an example of a relationship between the coordinate s and the radius of curvature r of the flexible tube portion 13. Next, the substantially straight portion on the proximal side of the flexible tube portion 13, namely, the coordinate s (sY) at which the radius of curvature r becomes substantially infinite is obtained. On the basis of the coordinate sp1 of the bend variation point P1 and the coordinate sY of the substantially straight area, the position of the coordinate s (s2) of the boundary P2 is defined as s2=(sp1−sY)/2.

(Calculation Method 2)

Figure 17:
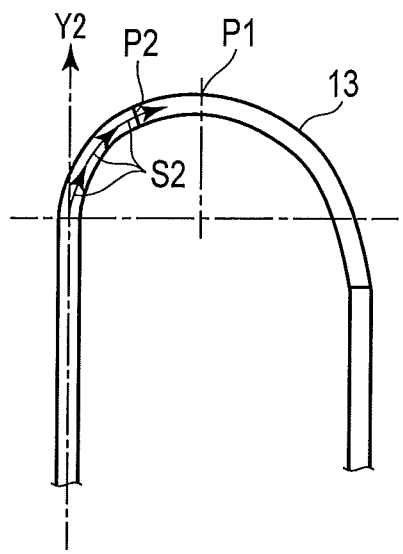
FIG. 17 is a diagram schematically showing another example of a bending state of the insertion section (flexible tube portion) according to Variant 1 of the third embodiment.

As shown in FIG. 17, a longitudinal axis direction S2 (a two-dimensional or three-dimensional vector) of the flexible tube portion 13 and an insertion direction Y2 (a two-dimensional or three-dimensional vector) of the substantially straight portion on the proximal side are calculated, in regard to each segment. Next, an angle θ of the insertion direction Y2 relative to the longitudinal axis direction S2 is calculated. Let us assume that the position where the calculated angle θ is less than 45° is the boundary P2 (two-dimensional or three-dimensional coordinates). Alternatively, the bend variation point P1 is obtained. Let us assume that the position of the coordinate s that is defined by the derivative dr/ds=1 is the boundary P2, as shown in FIG. 18, where r denotes the radius of curvature of the flexible tube portion 13, and s denotes the coordinate going from the proximal side to the distal side along the central axis of the flexible tube portion 13.

The boundary P2 between the fifth variable area A5 and the sixth variable area A6 calculated using Calculation Method 1 or 2 may be on the proximal side relative to the bend variation point P1 (see FIGS. 15 and 17). Thus, the fifth variable area A5, which has a relatively high stiffness, covers a wide range in the first variable area A1. When the fifth variable area A5 already abuts on the S-top and the sixth variable area A6 is bent, the force can be efficiently transmitted in the direction of passage by increasing the bending stiffness value of the fifth variable area A5, which covers a relatively wide range.

Thus, by dividing the first variable area A1 into at least the fifth variable area A5 and the sixth variable area A6 on the basis of the boundary P2, which is not limited to the bend variation point P1 and may be variously set, different levels of bending stiffness can be set in the first variable area A1.

Third Embodiment: Variant 2

According to the third embodiment, two variable stiffness areas (the fifth variable area A5 and the sixth variable area A6) are set in the first variable area A1; however, the number of variable stiffness areas to be set is not limited thereto. In the third embodiment, three or more variable stiffness areas may be set in the first variable area A1, using the concepts of obtaining the bend variation point P1 according to the third embodiment and obtaining the boundary P2 according to Variant 1 of the third embodiment. An example of setting four variable stiffness areas in the first variable area A1 by the variation point calculation section 37 will be described with reference to FIG. 19.

(Method of Calculating Four Variable Stiffness Areas)

First, the bend variation point P1 is calculated as described above. Next, the boundary P2 is calculated using Calculation Method 1 or 2 described in Variant 1. Let us assume that the boundary P2 is on the proximal side relative to the bend variation point P1. A boundary P3 is calculated, using Calculation Method 1 or 2 described with reference to Variant 1 again, from within the range extending from the bend variation point P1 to the distal end of the first variable area A1. In the above-described manner, the bend variation point P1 and the boundaries P2 and P3 are calculated from within the first variable area A1.

Let us assume that the area extending from the most distal segment in the first variable area A1 to a segment including the boundary P3 is a second variable area A12. Let us assume that the area extending from a proximal-side segment adjacent to the segment including the boundary P3 to a segment including the bend variation point P1 is a third variable area A13. Let us assume that the area extending from the proximal-side segment adjacent to the segment including the bend variation point P1 to a segment including the boundary P2 is a fourth variable area A14. Let us assume that the area extending from a proximal-side segment adjacent to the segment including the boundary P2 to the most proximal segment in the first variable area A1 is a fifth variable area A15. Let us also assume that the area located at the distal side relative to the first variable area A1 is a sixth variable area A16, and that the area located at the proximal side relative to the first variable area A1 is a seventh variable area A17.

Assuming that the bending stiffness values of the second to seventh variable areas A12 to A11 are K12 to K17, respectively, the variable stiffness control section 35 controls the bending stiffness of the variable stiffness element 60 of each area in real time so as to be defined, for example, as follows: K12>K13<K14>K15, K13<K16, and K15<K17. On the distal side relative to the boundary P2, the bending stiffness of the variable stiffness element 60 of each area is controlled by the variable stiffness control section 35, in such a manner that the stiffness decreases from the second variable area A12 to the third variable area A13 immediately following thereafter, namely, as the curvature increases. In the range between the boundary P3 and the boundary P2, the bending stiffness is controlled in such a manner that the stiffness increases from the third variable area A13 on the distal side t the fourth variable area A14 on the proximal side. On the proximal side relative to the bend variation point P1, the bending stiffness is controlled in such a manner that the stiffness decreases from the fourth variable area A14 to the fifth variable area A15, but increases again from the fifth variable area A15 to the seventh variable area A17.

The method for setting the bending stiffness of each area is not limited thereto. It is to be noted, however, that its basic concept is to decrease the bending stiffness value of an area (segments) that is greatly bent (e.g., make the bending stiffness value K13 of the third variable area A13 minimum in the first variable area A1). If two bent areas are adjacent to each other, the bending stiffness value of one of the areas that is in the direction of passage (on the distal side) is set to be higher than the other (e.g., the relationship between the bending stiffness value K12 of the second variable area A12 and the bending stiffness value K13 of the third variable area A13, or the relationship between the bending stiffness value K14 of the fourth variable area A14 and the bending stiffness value K15 of the fifth variable area A15).

The flexible tube portion 13 (e.g., the third variable area A13) that has passed through the S-top is pressed against the intestinal tract in the transverse direction. In the present variant, the pressing force against the intestinal tract can be reduced by softening the portion of the flexible tube portion 13 that is pressed in the transverse direction. Furthermore, by setting the bending stiffness of the second variable area A12 on the distal side to be higher than that of the third variable area A13, the force toward the distal end is increased, thus facilitating transmission of the force in the direction of passage. It is thus possible to provide a flexible tube insertion apparatus that is safe for patients and ensures the ease of insertion.

According to the present variant, since three or more (four in the present variant) variable stiffness areas are set in the first variable area A1, and the variable stiffness element 60 is controlled in such a manner that the variable stiffness control section 35 changes the bending stiffness of the variable stiffness element 60 included in each area, it is possible to perform variable stiffness control that is more appropriately suited to various shapes of flexure on different occasions within the first variable area A1.

The present invention has been described above based on the embodiments and the variants thereof, but the present invention is not limited to those embodiments. The present invention may be modified and changed in various manners, without departing from the spirit and scope of the invention. For example, the flexible tube insertion apparatus is not limited to the endoscope apparatus 1, and includes a wide range of insertion apparatuses comprising a flexible insertion section.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an insertion section having a distal side configured to be inserted into a subject;
   a first variable stiffness actuator provided in the insertion section and configured to change a stiffness of the insertion section; and
   a controller configured to:
      receive an indication of a bend shape of the insertion section;
      control, based on the received bend shape of the insertion section, the first variable stiffness actuator to change the stiffness of the insertion section;
      determine, when the received bend shape includes a single bend in the insertion section, whether the single bend has a curvature equal to or greater than a predetermined curvature; and
      when the single bend is determined to have a curvature equal to or greater than the predetermined curvature, control the first variable stiffness actuator to make a stiffness at a distal portion of the single bend greater than a stiffness at a proximal portion of the single bend.

2. The endoscope system according to claim 1, further comprising a second variable stiffness actuator provided in the insertion section in the proximal portion of the single bend,
   wherein, when the single bend is determined to have a curvature equal to or greater than the predetermined curvature, the controller is configured to control the first variable stiffness actuator and the second variable stiffness actuator such that the stiffness of the distal portion of the single area is higher than the stiffness of the proximal portion of the single area.

3. The endoscope system according to claim 1, further comprising a shape acquisition device that detects the bend shape of the insertion section.

4. The endoscope system according to claim 3, wherein the shape acquisition device acquires the bend shape of the insertion section by real-time detection, and the controller performs the control in real time based on the shape of the insertion section acquired by the shape acquisition device.

5. A stiffness control apparatus of an endoscope, the endoscope including an insertion section having a distal side configured to be inserted into a subject; and a first variable stiffness actuator provided in the insertion section and configured to change a stiffness of the insertion section, the control apparatus comprising:

a controller configured to:
receive an indication of a bend shape of the insertion section;
control, based on the received bend shape of the insertion section, the first variable stiffness actuator to change the stiffness of the insertion section;
determine, when the received bend shape includes a single bend in the insertion section, whether the single bend has a curvature equal to or greater than a predetermined curvature; and
when the single bend is determined to have a curvature equal to or greater than the predetermined curvature, control the first variable stiffness actuator to make a stiffness at a distal portion of the single bend greater than a stiffness at a proximal portion of the single bend.

6. The endoscope system of claim 1, wherein the first variable stiffness actuator is a first variable stiffness material.

7. The endoscope system of claim 6, wherein the first variable stiffness material is an electroactive polymer artificial muscle.

8. The endoscope system of claim 2, wherein each of the first variable stiffness actuator and the second variable stiffness actuator is a first variable stiffness material.

9. The endoscope system of claim 8, wherein the first variable stiffness material is an electroactive polymer artificial muscle.

10. The control apparatus of claim 5, wherein the first variable stiffness actuator is a first variable stiffness material.

11. The control apparatus of claim 10, wherein the first variable stiffness material is an electroactive polymer artificial muscle.

12. An endoscope system comprising:
an insertion section having a distal side configured to be inserted into a subject;
a plurality of variable stiffness actuators provided in the insertion section and each configured to change a stiffness of a corresponding portion of the insertion section; and
a controller configured to:
receive an indication of a bend shape of the insertion section;
determine whether a stiffness of the insertion section corresponding to the bend shape should be changed in order to facilitate insertion of the insertion section;
when it is determined that the stiffness of the insertion section corresponding to the bend shape should be changed, determining if the bend shape has a first portion whose stiffness should be changed differently from a stiffness of a second portion of the bend shape; and
when it is determined that the stiffness of the first portion should be changed differently from the stiffness of a second portion of the bend shape, controlling one or more variable stiffness actuators of the plurality of variable stiffness actuators in the first portion to have a different stiffness than one or more variable stiffness actuators of the plurality of variable stiffness actuators in the second portion.

13. The endoscope system according to claim 12, further comprising a shape acquisition device that detects a shape-of the insertion section and outputs the indication of the bend shape of the insertion section to the controller.

14. The endoscope system according to claim 12, wherein the shape acquisition device acquires the shape of the insertion section by real-time detection, and the controller performs the determination of whether a stiffness of the insertion section corresponding to the bend shape should be changed in order to facilitate insertion of the insertion section in real time.

15. The endoscope system according to claim 12, wherein the determination of whether the stiffness of the insertion section corresponding to the bend shape should be changed in order to facilitate insertion of the insertion section is based on whether the bend shape has a curvature greater than a predetermined curvature.

16. The endoscope system according to claim 15, wherein the determination of whether the bend shape has a first portion whose stiffness should be changed differently from the stiffness of a second portion of the bend shape is based on whether the first portion has a curvature greater than a curvature of the second portion.

17. The endoscope system according to claim 16, wherein an apex of the bend shape is included in the first portion.

18. The endoscope system according to claim 17, wherein the apex corresponds to an S-top of a sigmoid colon of the subject.

19. The endoscope system according to claim 15, wherein when the first portion has a greater curvature than the second portion, the first portion is distally arranged relative to the second portion and the one or more variable stiffness actuators of the plurality of variable stiffness actuators in the first portion are controlled to have a greater stiffness than the one or more variable stiffness actuators of the plurality of variable stiffness actuators in the second portion.

20. A stiffness control apparatus of an endoscope, the endoscope including an insertion section having a distal side configured to be inserted into a subject and a plurality of variable stiffness actuators provided in the insertion section, each configured to change a stiffness of a corresponding portion of the insertion section, the control apparatus comprising:
a controller configured to:
receive an indication of a bend shape of the insertion section;
determine whether a stiffness of the insertion section corresponding to the bend shape should be changed in order to facilitate insertion of the insertion section;
when it is determined that the stiffness of the insertion section corresponding to the bend shape should be changed, determining if the bend shape has a first portion whose stiffness should be changed differently from a stiffness of a second portion of the bend shape; and
when it is determined that the stiffness of the first portion should be changed differently from the stiffness of a second portion of the bend shape, controlling one or more variable stiffness actuators of the plurality of variable stiffness actuators in the first portion to have a different stiffness than one or more variable stiffness actuators of the plurality of variable stiffness actuators in the second portion.

21. The control apparatus according to claim 20, wherein the determination of whether the stiffness of the insertion section corresponding to the bend shape should be changed in order to facilitate insertion of the insertion section is based on whether the bend shape has a curvature greater than a predetermined curvature.

22. The control apparatus according to claim 21, wherein the determination of whether the bend shape has a first portion whose stiffness should be changed differently from the stiffness of a second portion of the bend shape is based on whether the first portion has a curvature greater than a curvature of the second portion.

23. The control apparatus according to claim 22, wherein an apex of the bend shape is included in the first portion.

24. The control apparatus according to claim 23, wherein the apex corresponds to an S-top of a sigmoid colon of the subject.

25. The control apparatus according to claim 22, wherein when the first portion has a greater curvature than the second portion, the first portion is distally arranged relative to the second portion and the one or more variable stiffness actuators of the plurality of variable stiffness actuators in the first portion are controlled to have a greater stiffness than the one or more variable stiffness actuators of the plurality of variable stiffness actuators in the second portion.

* * * * *